United States Patent [19]
Milkowski et al.

[11] 4,038,306
[45] July 26, 1977

[54] N-T-BUTOXYCARBONYL-S-LOWER ALKANOYLAMIDOMETHYL-CYSTEINE AND P-NITROPHENYL ESTERS

[75] Inventors: John D. Milkowski, Edison, N.J.; Daniel F. Veber, Ambler; Ralph F. Hirschmann, Blue Bell, both of Pa.

[73] Assignee: Merck & Co., Inc., Rahway, N.J.

[21] Appl. No.: 616,110

[22] Filed: Sept. 23, 1975

Related U.S. Application Data

[60] Continuation-in-part of Ser. No. 384,532, Aug. 1, 1973, abandoned, which is a division of Ser. No. 57,883, June 17, 1970, Pat. No. 3,770,822, which is a division of Ser. No. 658,665, Aug. 7, 1967, Pat. No. 3,560,521.

[51] Int. Cl.$^2$ .............. C07C 149/24; C07C 149/243
[52] U.S. Cl. .................... 260/479 S; 260/112.5 R; 260/112.7; 260/470; 260/481 C; 260/516; 260/534 S

[58] Field of Search .................. 260/481 C, 479 S

[56] References Cited
U.S. PATENT DOCUMENTS

| | | | |
|---|---|---|---|
| 3,448,141 | 6/1969 | Marinier | 260/481 C |
| 3,532,736 | 10/1970 | Chamberlin | 260/481 C |
| 3,711,458 | 1/1973 | Olofson et al. | 260/481 C |
| 3,769,271 | 10/1973 | Southard | 260/479 S |
| 3,855,238 | 12/1974 | Batesky et al. | 260/481 C |

Primary Examiner—Vivian Garner

[57] ABSTRACT

Novel protecting groups for peptides containing a cysteine residue. Process for the synthesis of peptides containing a cysteine residue wherein the mercapto function of the cysteine residue is protected by an acetamidomethyl radical or other labile blocking group. Novel intermediates useful in peptide synthesis.

3 Claims, No Drawings

N-T-BUTOXYCARBONYL-S-LOWER ALKANOYLAMIDOMETHYL-CYSTEINE AND P-NITROPHENYL ESTERS

This is a continuation-in-part of Ser. No. 384,532, filed Aug. 1, 1973, now abandoned, which is a division of Ser. No. 57,883, filed June 17, 1970, now U.S. Pat. No. 3,770,822, issued Nov. 6, 1973 which, in turn, is a divisional of Ser. No. 658,665, filed Aug. 7, 1967, now U.S. Pat. No. 3,560,521, issued Feb. 2, 1971.

Peptides containing cysteine, such as glutathione, insulin, oxytocin, or ribonuclease, are generally synthesized with the mercapto function protected by some appropriate group. Several protecting groups are known in the art which are useful in the synthesis of peptides containing a cysteine residue, but many of the known protecting groups are removed with great difficulty during the final stages of the synthesis or are unstable to some of the reagents generally employed in peptide synthesis. By the present invention, novel blocking groups for cysteine are provided which are stable to most of the reagents and general reaction conditions employed in peptide synthesis but are easily removed by specific reagents.

Peptides containing cysteine with the unprotected mercapto function have rarely been synthesized due to the difficulty in separating the resulting compound from the by-products formed by oxidation. During the synthesis of peptides with the unprotected mercapto function, dehydrogenation to cysteine derivatives occurs very readily, and this often leads to further complications. Cysteine is, therefore, employed almost exclusively in its S-protected form in the synthesis of pepetides containing a cysteine residue, and for this reason it is desirable to have a suitable blocking group which can be easily removed during synthesis but which is also stable to reagents and reaction conditions generally employed in peptide synthesis.

By this invention, novel blocking groups are provided which combine the properties of ease of removability and stability to the general reaction conditions employed in the synthesis of peptides and, in particular, in the synthesis of peptides containing one or more cysteine residues, such as glutathione, insulin, oxytocin, or ribonuclease.

Many peptides are known to be biologically active. Some are useful in the study and analysis of proteins, particularly in studies designed to gain insight into the physiological action of enzymia, hormones and other proteins with important functions in the body. Insulin, for example, occupies the key position in the hormonal regulation of the sugar balance, and a deficiency of insulin causes the metabolic malfunction diabetes mellitus; oxytocin, a cyclic nonapeptide with a 20-membered disulfide ring, stimulates milk ejection in the lactating mammary gland, and it is often used therapeutically to induce labor. Vasopressin has been used as substitution medication in the case of diabetes insipidus and to treat anenteroneuria.

The most commonly applied protection group for the mercapto function is the S-benzyl group. The S-benzyl blocking group generally decreases the solubility of the peptide in hydroxylic solvents. Cleavage of this group is achieved, however, only through the use of sodium in liquid ammonia. This system leads to the decomposition of many peptides. Hydrogen fluoride has been employed to remove the S-benzyl blocking group but is unsuitable because it is impractical for large scale preparation, often causes destruction of the peptide and is not sufficiently selective, since it will also remove the carbobenzoxy, t-butoxy and t-butoxycarbonyl groups. Other groups such as the S-p-nitrobenzyl, S-p-diphenylmethyl, S-benzylthiomethyl, and the triphenylmethyl groups have been employed in the synthesis of cysteine peptides, but they too are not entirely satisfactory. The p-nitorphenyl group, for example, decreases the solubility of the peptide in hydroxylic solvents and is only removed through the use of catalytic hydrogenation in the presence of palladium-on-charcoal and hydrochloric acid. This system does not work well in the presence of sulfur since the catalyst is often poisoned during the reaction and does not allow any selectivity if a carbobenzoxy group is present elsewhere in the molecule since this group will also be removed by this system. In the case of S-benzylthiomethyl-cysteine, the protecting group can be removed with mercuric chloride in warm hydrochloric acid or mercuric acetate in 80% formic acid. Strongly acid conditions are undesirable since it destroys groups containing tryptophan and causes the formation of undesirable by-products. The presence of this group also decreases the solubility of the peptide in hydroxylic solvents. The S-p-diphenylmethyl group can be removed by sodium in liquid ammonia or trifluoroacetic acid. The latter reagent is also unsuitable since it is not selective and will also remove the t-butyl esters and the t-butoxycarbonyl groups. The presence of a strong acid is another undesirable feature. The triphenylmethyl group can be removed in mild acid or with mercury salts, but this blocking group is too easily removed with mild acid under conventional conditions, thus making it an unsatisfactory blocking group for peptide synthesis. In addition, the presence of this group decreases the solubility of the peptide in hydroxylic solvents.

The S-blocking groups which are the subject of this invention may be depicted as follows using the cysteine molecule as an example of a cysteine residue:

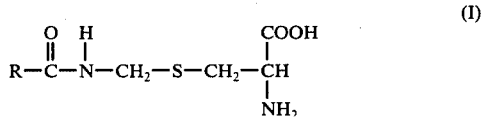

(I)

where R represents loweralkyl, such as methyl, ethyl, propyl and butyl, aryl, such as phenyl or naphthyl, or an acetonyl or benzyloxy radical.

Where R in Formula I equals loweralkyl or aryl, the blocking group can be formed in a 2-step reaction. The first step involves the formation of a N-hydroxymethylalklamide or N-hydroxymethyl-arylamide, for example, N-hydroxymethyl-acetamide or N-hydroxymethyl-benzamide, via reaction of about equimolar amounts of an amide, such as acetamide or benzamide, and formaldehyde in the presence of a catalytic amount of potassium carbonate. For convenience, a 36 –38% aqueous formaldehyde solution can be employed. This mixture is heated for several minutes on a steam bath and is then generally allowed to stand several hours at room temperature. Dry ice is added to introduce carbon dioxide into the solution, after which the solution is evaporated in vacuo at a bath temperature of about 40° –50° C. The residue is dissolved in a suitable solvent, such as acetone or methylene chloride, the solution is dried over a suitable drying agent, and the solvent is removed in vacuo.

The residue is purified by crystallization or other techniques known in the art.

In the second step, cysteine hydrochloride monohydrate and a slight excess of the N-hydroxymethyl-alkylamide or N-hydroxymethyl-arylamide are dissolved in a suitable solvent, such as water, methanol, or ethanol. The reaction probably proceeds through an intermediate such as that depicted in the following reaction scheme:

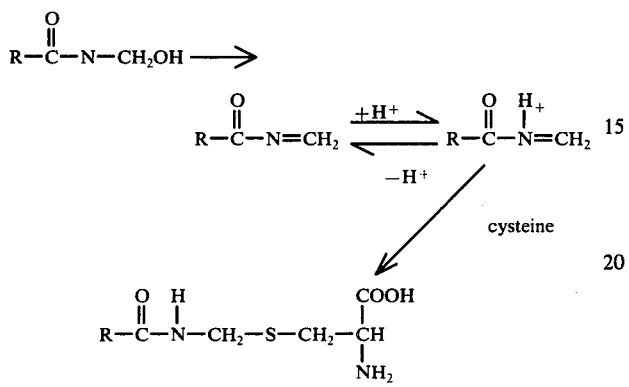

where R is loweralkyl, aryl, or benzyloxy. The solution of the reactants is cooled in an ice bath, and an acid, such as concentrated hydrochloric acid, hydrobromic acid or sulfuric acid, is added with stirring. The reaction mixture is then sealed, preferably under an inert atmosphere such as nitrogen, for example, and is allowed to stand at room temperature for several hours or up to 1 – 2 days. The use of nitrogen is not a critical feature, but its use generally leads to better yields of the desired product. The mixture is then evaporated in vacuo at about 40° – 50° C. A solvent, such as benzene or ethanol, is added and subsequently removed to remove traces of water, and the solid residue is recrystallized from a suitable solvent, such as methanol or ethanol, or mixtures of alcohol and anhydrous ether. The product is obtained as its acid salt, and the absence of free cysteine in the 5-alkylamidomethylcysteine salt is determined by thin layer chromatography. The free amino acid can be obtained by treating the acid salt with aqueous alkali until the solution is just at the isoelectric point, or by adding silver oxide to remove chloride ion as silver chloride.

Where R in Formula I equals benzyloxy, the blocking group may be formed in a manner similar to that described above. N-hydroxymethyl-benzyloxycarboxamide is prepared by reacting benzyloxycarboxamide with formaldehyde, and the blocking group is attached by reacting approximately equimolar amounts of cysteine hydrochloride monohydrate with N-hydroxymethylbenzyloxy-carboxamide to yield the acid salt of S-[benzyloxycarboxamidomethyl]-cysteine. The absence of free cysteine in the product is determined by thin layer chromatography.

Where R in Formula I equals acetonyl, the methyl compound is formed by reacting approximately equimolar amounts of S-methyl-isoxazole and formaldehyde in the presence of an equivalent amount of hydrochloric acid. The procedure described above is essentially repeated to yield 2-hydroxy-methyl-5isoxazolium chloride. The latter compound is reacted with cysteine hydrochloride monohydrate in the presence of an acid such as hydrochloric acid or hydrobromic acid to form a condensation product which is isolated but not purified. The condensation product is treated with aqueous alkali which causes the oxazole ring to open and the product, S-[acetoacetamidomethyl]-cysteine, is obtained.

Alternatively, the S-alkylamidomethylcysteine compounds can be prepared using derivatives of N-hydroxymethylalkylamides, such as the esters, or halomethylalkylamides. The esters can be conveniently prepared from the N-hydroxymethyl-alkyl or aryl- amides by reaction with acylating agents such as acetyl chloride, acetic anhydride, trifluoroacetic anhydride, methanesulfonyl chloride, or p-toluenesulfonyl chloride.

The halo derivatives can be prepared from an appropriate amide, such as acetamide or benzamide by reaction with formaldehyde and dry hydrogen chloride or hydrogen bromide gas in a suitable solvent such as glacial acetic acid. Alternatively, the halomethyl derivatives can be prepared from the corresponding N-hydroxymethyl amide by reaction with phosphorus pentachloride or phosphorus tribromide in a suitable solvent, such as dioxane, or a mixture of ether and dioxane.

These derivatives can be reacted with cysteine over a broad pH range, under acidic or basic conditions, to form the corresponding S-alkyl- or S-aryl- amidomethylcysteine. For example, S-acetamidomethylcysteine can be prepared from O-methanesulfonyl-N-hydroxymethylacetamide by reaction with cysteine in a suitable solvent such as water or ethanol, or a mixture of solvents. The reaction is carried out at pH 5 and about equimolar amounts of the reactants are employed. The pH is controlled by addition of alkali such as sodium hydroxide. The product is purified, after removal of the solvent in vacuo, by recrystallization from methanol-ether, or by techniques known in the art.

The S-alkylamido blocking group can be completely removed from a peptide containing a cysteine residue by stirring about a molar equivalent of a water-soluble salt of a heavy metal, such as the acetate or nitrate salts of mercury, silver, cadmium, tin, antimony, platinum, gold, lead, and bismuth, or organo-metallic salts of heavy metals, such as p-chloromercuri-benzoic acid, with an aqueous solution of the S-alkylamidomethylcysteine for 1 – 2 hours. Solvents such as methanol, dimethylformamide or mixtures of these solvents may also be employed. The reaction is generally carried out at room temperature, although temperatures other than room temperature may also be employed. The solid metal salt is generally added to the solution of the cysteine derivative, but the salt can also be added in solution. A precipitate generally forms at this point, and the reaction is allowed to run for about 30 – 90 minutes. The reaction can be carried out over a broad pH range under acidic or basic conditions, depending upon the particular reagent employed to remove the blocking group. Best results are obtained, however, at pH 4 when inorganic salts are employed as the deblocking agent and at pH 9 when organo-metallic salts of heavy metals are employed as the deblocking agents. Where the salt is added in solution, the pH of the solution is generally preadjusted to the pH at which the reaction will be carried out. After the reaction is complete, hydrogen sulfide gas is added to the mixture to remove the metal or it may be removed by dialysis against chelating agents such as ethylenediamine tetraacetic acid. The total absence of the blocking group is determined by thin layer chromatography.

Where R equals acetonyl, the blocking group can be removed with hydroxylamine, hydrazine, or phenylhydrazine in glacial acetic acid at room temperature. The hydrazine adds across the two carbonyl functions to a form a cyclic hydrazide and the S-aminomethylcysteine residue. The latter residue is unstable in aqueous media, and addition of water or aqueous alcohol causes it to break up into ammonia, formaldehyde, and the free peptide. The product is generally precipitated with ether as the hydrobromide salt.

Where a disulfide linkage is desired in the peptide end-product, air is bubbled into the reaction mixture after removal of the blocking group, and the disulfide is formed by air oxidation.

These novel blocking groups are particularly useful in peptide synthesis since they have been found to be stable under the various reaction conditions generally employed in the synthesis of peptides. For example, the blocking groups are stable under acidic or basic conditions from pH 0 - 13, in concentrated ammonia, and in trifluoroacetic acid. S-acetamidomethylcysteine, which is an intermediate useful in the synthesis of cysteine-containing peptides, is highly water soluble, a property which is useful in some types of peptide synthesis.

The novel blocking groups can be used in the synthesis of known peptides which have generally known biological properties, such as oxytocin, which regulates lacatation, and vasopressin, which has hypertensive properties.

In the synthesis of oxytocin, for example, it has been found that the mercapto function can be protected by first reacting S-acetamidomethylcysteine-N-carboxyanhydride with prolyl-leucyl-glycine amide in the presence of potassium borate, at a pH of about 10 - 11; generally about a 1% molar excess of the carboxyanhydride is employed. After the addition of the N-carboxyanhydride, the pH is adjusted to about 3 with a mineral acid such as concentrated sulfuric acid, and the reaction vessel is flushed with nitrogen for about 15 minutes to remove carbon dioxide. The pH is then again adjusted to 10 - 11 with potassium hydroxide, after which asparagine-N-carboxyanhydride is added to the mixture. The above sequence in which the pH is lowered to 3 and raised back to 10 upon addition of the successive carboxyanhydrides is repeated during the addition of glutamine-N-carboxyanhydride, isolucine-N-carboxyanhydride, and tyrosine-N-carboxyanhydride, until the final step in the sequence is reached, where the pH is raised to about 8 and about 10% excess of N-t-butoxycarbonyl- S-acetamidomethylcysteine-N-hydroxysuccinimide ester is added. The pH is then lowered to and maintained at 1 for about 15 - 20 hours, in order to remove the t-butoxycarbonyl group, and the S-acetamidomethyl blocking group is removed upon the addition of mercury acetate at a pH of about 4 - 5. Hydrogen sulfide gas is bubbled into the mixture to remove the mercury, after which air is bubbled in to oxidize the residue to oxytocin. It has also been found that in place of N-t-butoxycarbonyl-S-acetamidomethylcysteine-N-hydroxysuccinimide ester it is possible to use N-o-nitrophenylsulfenyl-S- acetamidomethylcysteine-p-nitrophenyl ester to obtain the final product.

S-acetamidomethylcysteine-N-carboxyanhydride is prepared by reacting S-acetamidomethylcysteine with phosgene in a suitable dry solvent, such as peroxide-free tetrahydrofuran. The phosgene is bubbled into the reaction mixture with stirring, and at the end of the reaction period a clear solution is obtained. The product is recovered upon evaporation of the solvent and is purified by techniques known in the art.

N-t-butoxycarbonyl-S-acetamidomethylcysteine-N-hydroxysuccinimide ester can be prepared by reacting N-t-butoxycarbonyl-S-acetamidomethylcysteine with N-hydroxysuccinimide in a suitable solvent such as dry dioxane. N-t-butoxycarbonyl-S-acetomidomethylcysteine can be prepared by reacting S-acetamidomethylcysteine with t-butoxycarbonylazide in a suitable solvent, such as dioxane, in the presence of a base, such as magnesium oxide.

Similarly, other N-t-butoxycarbonyl-S-loweralkylamidomethylcysteine derivatives can be made by using the cysteine derivatives of formula (I) wherein R represents lower alkyl in the above process. The p-nitrophenyl esters of the above N-t-butoxycarbonyl-S-alkylamidomethylcysteine compounds can be prepared by reacting the above compounds with p-nitrophenyl in the presence of an excess of dicyclohexylcarbodiimide. For example, N-t-butoxycarbonyl-S-acetamidomethylcysteine p-nitrophenyl ester can be prepared by reacting N-t-butoxycarbonyl-S-acetamidomethylcysteine with p-nitrophenol as indicated above. N-o-nitrophenylsulfenyl-S-acetamidomethylcysteine-p-nitrophenyl ester can be prepared by reacting N-o-nitrophenysulfenyl-S-acetamidomethylcysteine with nitrophenol in a suitable solvent such as tetrahydrofuran in the presence of an excess of dicyclohexylcarbodiimide. N-o-nitrophenylsulfenyl-S-acetamidomethylcysteine can be prepared by reacting S-acetamidomethylcysteine with o-nitrophenylsulfenylchloride in a suitable solvent such as dioxane in the presence of a base such as magnesium oxide.

As can be seen from the above illustration, the novel blocking groups can be employed in the synthesis of a number of different peptides containing one or more cysteine residues. The demonstrated chemical stability of the novel blocking groups and the ease with which they are removed with specific reagents are distinct advantages over the blocking groups which are currently employed in peptide synthesis.

The following examples are given for purposes of illustration and not by way of limitation:

EXAMPLE 1

S-ACETAMIDOMETHYLCYSTEINE HYDROCHLORIDE 127 grams (1.43 mole) of N-hydroxymethylacetamide and 228 grams (1.3 mole) of cysteine hydrochloride monohydrate are dissolved in 350 ml. of water in a round-bottom flask. The solution is cooled in an ice bath and 50 ml. of concentrated hydrochloric acid are added slowly with stirring. Nitrogen gas is introduced into the flask, after which the flask is stoppered and allowed to stand for 2 days at room temperature. The reaction mixture is then evaporated in vacuo at 40° C. Absolute ethanol is added and evaporated in vacuo. This step is repeated several times to remove all traces of water. The resulting white solid is dissolved in methanol at room temperature, and anhydrous ether is added until the solution becomes cloudy. The solution is allowed to stand for 3 days at 0°- 5° C., during which the product crystallizes. After filtration, washing with ether, and drying in vacuo at room temperature, 150 grams of S-acetamidomethylcysteine hydrochloride, m.p. 187 dec., are obtained.

The free base is obtained by dissolving the hydrochloride in a small quantity of water and adding dilute sodium hydroxide until the isoelectric point is reached. The solvent is removed in vacuo, and the residue crystallized from ethanol. Alternatively, one equivalent of silver oxide is added to a water solution of the hydrochloride salt. The precipitated silver chloride is filtered off, the solvent is removed in vacuo, and the residue is crystallized from ethanol.

When in the above procedure N-hydroxy-methylpropionamide or N-hydroxymethylbenzamide are substituted for N-hydroxy-methylacetamide, there are obtained S-propionamidomethylcysteine hydrochloride and S-benzamidomethylcysteine hydrochloride, respectively.

EXAMPLE 2
N-TERTIARY BUTOXYCARBONYL-S-ACETAMIDOMETHYL-CYSTEINE 22.8 grams (0.1 mole) of S-acetamidomethylcysteine hydrochloride are dissolved in 250 ml. of 50% dioxane (peroxide-free) in a 500 ml. 3-neck flask equipped with a mechanical stirrer and condenser. 12 grams of magnesium oxide (0.3 mole) are added, and the mixture is stirred at room temperature for 30 minutes. 15.7 grams (0.11 mole) of redistilled t-butoxycarbonylazide are added, and the mixture is stirred for 20 hours in an oil bath at 45° C. The reaction mixture is then cooled to room temperature, and 1 liter of water is added. The aqueous mixture is washed with 2 × 250 ml. of ethyl acetate, cooled in an ice bath, and acidified to pH 3 with 50% citric acid. The acidic solution is then saturated with sodium chloride and extracted with ethyl acetate. The extracts are washed twice with 200 ml. of saturated sodium chloride solution, dried over anhydrous sodium sulfate, filtered, and evaporated in vacuo to yield an amorphous solid. The solid is dissolved in warm ethyl acetate, and 2 volumes of benzene are added. Upon standing at room temperature, the product crystallizes and, after filtration, is washed with benzene and dried in vacuo. A second and third crop are obtained by adding benzene to filtrates and seeding. After drying in vacuo, 11 grams of N-t-butoxycarbonyl-S-acetamido-methylcysteine, m.p. 110° – 112° C., are obtained.

When in the above procedure benzyloxycarbonylazide or ethoxycarbonylazide are substituted for t-butoxycarbonyl-azide, there are obtained benzoxycarbonyl-S-acetamidomethylcysteine and ethoxycarbonyl-S-acetamidomethylcysteine, respectively.

EXAMPLE 3
S-ACETAMIDOMETHYLCYSTEINE-N-CARBOXYANHYDRIDE 1.0 gram of S-acetamidomethylcysteine is placed in a dry, 3-neck flask containing a gas inlet tube and condenser with drying tube. 50 ml. of dry peroxide-free tetrahydrofuran are added, and the suspension is stirred while a stream of phosgene is introduced at room temperature. After 3 hours almost complete solution is achieved, and the solution is filtered and evaporated in vacuo to yield S-acetamidomethylcysteine-N-carboxyanhydride as a yellow oil. The oil is identified as the desired product by infrared spectra.

When in the above procedure S-propionamidomethylcysteine and S-p-chlorobenzamidomethylcysteine are used in place of S-acetamiodmethylcysteine, there are obtained S-propionamidomethylcysteine-N-carboxyanhydride and S-p-chlorobenzamidomethylcysteine-N-carboxyanhydride, respectively.

EXAMPLE 4
N-o-NITROPHENYLSULFENYL-S-ACETAMIDOMETHYLCYSTEINE-p-NITROPHENYL ESTER

N-o-Nitrophenylsulfenyl-S-acetamidomethylcysteine 22.8 grams (0.1 mole) of S-acetamidomethylcysteine hydrochloride are dissolved in 250 ml. of 50% peroxide-free dioxane in a 500 ml. 3-neck flask equipped with a mechanical stirrer and condenser. 12 grams (0.3 mole) of magnesium oxide are added, and the mixture is stirred for 30 minutes at room temperature. 0.11 mole of o-nitrophenylsulfenylchloride are added, and the mixture is stirred for 3 hours in an oil bath at 45° C. The reaction mixture is then cooled to room temperature, and 1 liter of water is added. The aqueous mixture is washed twice with 200 ml. of ethyl acetate, cooled in an ice bath, and acified to pH 3 with 50% citric acid. The solution is then saturated with sodium chloride and extracted with ethyl acetate. The extracts are washed twice with 200 ml. of saturated sodium chloride solution, dried over anhydrous sodium sulfate, filtered and evaporated in vacuo. The residue is crystallized from ethyl acetatebenzene.

When in the above procedure S-benzamidomethylcysteine hydrochloride and S-benzyloxycarboxamidomethylcysteine hydrochloride are used in place of S-acetamidomethyl-cysteine hydrochloride, there are obtained N-o-nitrophenylsulfenyl-S-benzamidomethylcysteine and N-o-nitrophenylsulfenyl-S-benzyloxycarboxamidomethylcysteine, respectively.

N-o-nitrophenylsulfenyl-S-acetamidomethylcysteine-p-nitrophenyl ester.

0.025 mole N-o-nitrophenylsulfenyl-S-acetamidomethylcysteine are dissolved in 100 ml. of peroxide-free tetrahydrofuran in a dry flask. The solution is cooled in an ice-salt bath, and 0.0025 mole of o-nitrophenyl are added. After solution is complete, a 10% molar excess of dicyclohexylcarbodiimide is added, the mixture is stirred for 1 hour in an ice-salt bath, and is then allowed to stand overnight at 0° – 5° C. The urea by-product is filtered off, and the filtrates are evaporated in vacuo. The residue is dissolved in ethyl acetate, washed once with 1 N sodium bicarbonate, then 3 times with saturated sodium chloride, dried over anhydrous sodium sulfate, and evaporated in vacuo. Crystallization from chloroform-ether yields essentially pure N-o-nitrophenylsulfenyl-S-acetamidomethylcysteine-p-nitrophenyl ester.

When in the above procedure N-o-nitrophenylsulfenyl-S-benzamidomethylcrysteine and N-o-nitrophenylsulfenyl-S-benzyloxycarboxamidomethylcysteine are employed in place of N-o-nitrophenylsulfenyl-S-acetamidomethylcysteine, there are obtained N-o-nitrophenylsulfenyl-S-benzamidomethylcysteine-p-nitrophenyl ester and N-o-nitrophenylsulfenyl-S-benzyloxy-carboxamidomethylcysteine-p-nitrophenyl ester, respectively.

EXAMPLE 5

O-METHANE-SULFONYL-N-HYDROXYMETHYLACETAMIDE 4.4 grams (.05 mole) of N-hydroxymethylacetamide are dissolved in 50 ml. of pyridine in a 100 ml. 3-neck flask equipped with a drying tube, dropping funnel, mechanical stirrer, and thermometer. The solution is cooled in an ice bath and .055 mole of methanesulfonyl chloride is added dropwise over a period of about 20 minutes while the temperature is maintained between 5° – 10° C. After several minutes, a precipitate forms, and the mixture is stirred at 5° – 10° C. for 1 hour and then for 4 hours at room temperature. The precipitated pyridine hydrochloride is filtered off, and the filtrate is evaporated in vacuo at 40° C., yielding an oily residue. The product, O-methanesulfonyl-N-hydroxymethylacetamide, is identified by infrared spectra.

When in the above procedure p-toluenesulfonyl chloride is used in place of methanesulfonyl chloride, o-p-toluenesulfonyl-N-hydroxymethylacetamide is obtained.

EXAMPLE 6

PREPARATION OF S-ACETAMIDOMETHYLCYSTEINE FROM O-METHANESULFONYL-N-HYDROXYMETHYLACETAMIDE 1.21 grams (.01 mole) of cysteine are dissolved in 20 ml. of water. The pH of the resulting solution is 5.0. To this solution is added with stirring a solution of 0.011 mole of O-methanesulfonyl-N-hydroxymethylacetamide dissolved in 10 ml. of ethanol. The pH is maintained at 5 by the addition of 0.5 N sodium hydroxide. After stirring for several hours, the presence of S-acetamidomethylcysteine is indicated by thin layer chromatography. The solvent is removed in vacuo, and the residue is re-crystallized from methanol-ether to yield pure S-acetamidomethylcysteine.

When in the above procedure O-p-toluenesulfonyl-N-hydroxymethlacetamide is used in place of O-methanesulfonyl-N-hydroxymethylacetamide, the desired product, S-acetamidomethylcysteine, is obtained.

EXAMPLE 7

The following example illustrates the removal of the S-acetamidomethyl blocking group:

96 mg. (0.5 mmole) of S-acetamidomethylcysteine are dissolved in 5 ml. of water, and the solution is adjusted to pH 4 with 0.25 N hydrochloric acid. To this is added a solution of 159 mg. (0.5 mmole) of mercuric acetate in 5 ml. of water, which has previously been adjusted to pH 4. Upon mixing, a precipitate forms immediately. The pH drops and is adjusted to pH 4 for one hour. 2 ml. samples are withdrawn at 15-minute intervals during the reaction period. Hydrogen sulfide gas is added to each sample to stop the reaction. The clear, supernatant liquid is decanted off, and a thin layer chromatogram of each of the samples is run in a butanolacetic acid-water system. The samples removed after 30 and 45 minutes contain no S-acetamidomethylcysteine. The only products obtained are cysteine and cystine.

EXAMPLE 8

The following is an illustration of the use of the S-acetamido blocking group in the synthesis of a cysteine-containing peptide:

SYNTHESIS OF OXYTOCIN 2 mmoles of prolyl-leucyl-glycine amide and 20 cc. of potassium borate buffer (pH 10.2) are placed in a Waring Blender at 0° C. To this is added a 1% molar excess of S-acetamidomethylcysteine-N-carboxy anhydride with stirring. The pH is adjusted to 3.0 with concentrated sulfuric acid, and the system is flushed with nitrogen for 15 minutes to remove carbon dioxide. The pH is then raised to 10.2 with 50% potassium hydroxide and a 2% molar excess of asparagine-N-carboxyanhydride is added. The pH is adjusted to 3.0 with concentrated sulfuric acid, and the system is again flushed with nitrogen. The pH is then raised to 10.2 with 50% potassium hydroxide and a 3% excess of glutamine-N-carboxy anhydride is added. The pH is then lowered to 3 with concentrated sulfuric acid, and the system is flushed with nitrogen. The pH is then raised to 10.2 with 50% potassium hydroxide, and a 5% excess of tyrosine-N-carboxyanhydride is added. The pH is adjusted to 3 with concentrated sulfuric acid, and the system is again flushed with nitrogen to remove carbon dioxide. The pH is then raised to 8.0 with 50% potassium hydroxide, and a 10% molar excess of N-t-butoxycarbonyl-S-acetamidomethylcysteine-N-hydroxy succinimide ester is added. The pH is then lowered to 1 with concentrated sulfuric acid and is maintained at 1 for 15 hours to remove the tertiary butoxycarbonyl group. The pH is adjusted to 4, and a 10% molar excess of an aqueous solution of mercuric acetate is added to the reaction mixture. The pH is maintained at 4 by addition of sulfuric acid. Hydrogen sulfide gas is introduced into the reaction mixture to remove mercury ion, and air is bubbled into the reaction mixture to oxidize the product to oxytocin. The product is purified by chromatography over silica gel.

What is claimed is:

1. A compound of the formula

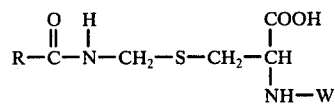

and p-nitrophenyl esters thereof, wherein R is lower alkyl, and W is t-butoxycarbonyl.

2. N-t-butoxycarbonyl-S-acetamidomethylcysteine.

3. N-t-butoxycarbonyl-S-acetamidomethylcysteine p-nitrophenyl ester.

* * * * *